United States Patent [19]

Thieler

[11] Patent Number: 5,026,389
[45] Date of Patent: Jun. 25, 1991

[54] METHOD AND APPARATUS FOR OPENING AND CLOSING SURGICAL WOUNDS

[76] Inventor: William R. Thieler, 2175 Via Tuscany, Winter Park, Fla. 32789

[21] Appl. No.: 604,059

[22] Filed: Oct. 26, 1990

Related U.S. Application Data

[62] Division of Ser. No. 225,377, Jul. 28, 1988, Pat. No. 4,966,605.

[51] Int. Cl.$^5$ ..................... A61B 17/00; A61L 15/00
[52] U.S. Cl. ..................................... 606/215; 128/156
[58] Field of Search ....................... 606/214, 215, 216; 128/155, 156

[56] References Cited

U.S. PATENT DOCUMENTS

| | | | |
|---|---|---|---|
| 2,018,517 | 10/1935 | Fetter | 606/215 |
| 2,421,193 | 5/1947 | Gardner | 606/215 |
| 2,735,426 | 2/1956 | Claydon | 128/156 |
| 3,060,932 | 10/1962 | Pereny et al. | 606/215 |
| 3,349,765 | 10/1967 | Blanford | 128/156 |
| 3,520,306 | 7/1970 | Gardner et al. | 606/215 |
| 3,921,627 | 11/1975 | Wilson | 128/156 |
| 4,370,981 | 2/1983 | Sanderson | 606/215 |
| 4,531,521 | 7/1985 | Haverstock | 606/215 |
| 4,653,492 | 3/1987 | Parsons | 128/155 |
| 4,743,232 | 5/1988 | Kruger | 128/156 |

Primary Examiner—Stephen C. Pellegrino
Assistant Examiner—Gary Jackson

[57] ABSTRACT

A surgical method and apparatus for opening and closing surgical wound utilizes an elastic member which is adhered across the patient's skin at the treatment site. The wound is opened by cutting through the elastic member and through the patient's skin to permit a surgical procedure to be conducted. The wound is then closed by reapproximating the patient's skin at the treatment site and by bringing the cut edges of the elastic member together and adhering a relatively inelastic sealing member over the elastic member to maintain the cut edges while the wound heals.

15 Claims, 2 Drawing Sheets

METHOD AND APPARATUS FOR OPENING AND CLOSING SURGICAL WOUNDS

This is a division of application Ser. No. 07/225,377, filed July 28, 1988, now U.S. Pat. No. 4,966,605.

BACKGROUND OF THE INVENTION

The present invention relates to surgical methods and apparatus, and in particular relates to methods and apparatus designed to open and close surgical wounds without using sutures, staples or other devices extending into the patient's body.

A variety of suture materials have been used in the past for closing surgical wounds. In recent times, staples have been utilized as a substitute for sutures. There have also been suggestions for using straps, buttons, zippers and glues to achieve these same ends.

It is now known that a surgical wound closure technique that extends a foreign substance into the patient's body (as sutures, staples, etc.) creates a higher likelihood of introduction of undesirable bacteria into the patient's body, thus increasing the incidence of infection.

There have been techniques which have been described for avoiding the use of devices which extend into the patient's body. For example, the use of Steri-Strips has been suggested to approximate the edges of the skin at the wound site, without the use of skin sutures, clips or staples, with lower infection rate being experienced. See *Surgical Practice News*, May 1988, p. 21. See also U.S. Pat. No. 4,038,989 to Romero-Sierra et al.

It is also preferable to avoid the use of sutures, staples and the like for purposes of reducing the amount of scar tissue forming at the surgical wound. There have been suggestions in the prior art for utilizing non-invasive materials for that purpose; see, for example, U.S. Pat. No. 3,847,155 to Bernaola, which teaches the use of a co-polymer film applied to the skin and over the wound.

Other techniques which have been suggested for avoiding the necessity of utilizing intrusive materials include surgical dressings which are attached on opposite sides of the wound, and which are in turn joined together by sutures, zippers or similar fasteners. See, for example, U.S. Pat. No. 2,752,921 to Fink.

SUMMARY OF THE INVENTION

The present invention is directed to a method and apparatus which is designed to assist in both opening and closing a surgical wound at the treatment site for purposes of reducing the potential for infection and the amount of scar tissue present in the wound following healing, as well as to achieve other benefits described in greater detail below.

In general terms, the method of the present invention contemplates the use of an elastic member which is adhered across the patient's skin at the treatment site. The surgical wound is then opened by cutting through the elastic member and the patient's skin at the site, and conducting a surgical procedure in the wounds. Thereafter the patient's skin is reapproximated at the treatment site by bringing the cut edges of the elastic member together and adhering a sealing member to the elastic member to maintain the cut edges of the elastic member together while the surgical wound heals.

It is preferred, although not required, that both the elastic member and the sealing member be formed of transparent materials so as to permit observation of the treatment site before the wound is opened and after the wound is closed.

The elastic member preferably comprises an elongated sheet of an elastic material which has an elastic adhesive along one surface, is relatively impervious to blood and body fluids, and has an elastic memory. Suitably, the elastic sheet has a dimension longer than the surgical wound, so as to leave uncut the ends of the elastic sheet. The sealing member preferably comprises a sheet dimensioned to fit on the exposed surface of the elastic sheet. Further, the sealing sheet is relatively inelastic with respect to the elastic sheet and has an adhesive along one surface thereof for adhering to the exposed surface of the elastic sheet across both the uncut and cut portions of the elastic sheet.

The specific materials selected for use with the elastic and sealing sheets, as well as the applied adhesives, form an important part of this invention. As noted above, the elastic sheet has an elastic memory and is relatively impervious to blood and body fluids. To this end, the elastic sheet is selected so as to have a non-tear and elastic memory characteristic capable of withstanding stretching to about twice its original dimensions. This permits the elastic sheet to be subjected to significant retraction along with the patient's skin, so as to open the surgical wound and permit the surgery to be conducted. Afterwards, the elastic memory is utilized to reapproximate the original position of the edges of the cut skin, even when the wound has been left open for a substantial period of time (for example, under septic conditions in the wound where the wound must be left open and closed at a later date). The sealing sheet preferably comprises a semi-rigid polyurethane or similar material which will not stretch appreciably following application to the exposed surface of the elastic sheet.

The adhesive applied to the bottom of the elastic sheet is specifically selected to preferably provide the following characteristics: a high moisture-vapor barrier for the elastic sheet; a high degree of elasticity, so as to expand and retract with the elastic sheet during the surgical procedure; and a high degree of adhesive "aggressiveness", for a few days following surgery. The adhesive applied to the bottom of the sealing sheet is selected to have a substantially greater aggressiveness than the elastic sheet adhesive, and is preferably initially removable (as, for example, pressure sensitive) if the sealing sheet needs repositioning.

Other features are available with the method and apparatus utilized in the present invention. For example, when a closed-cell foam is used for the elastic sheet, the closed-cell foam may be impregnated with an antiseptic material or other medicine to promote wound treatment. Another feature contemplated is the utilization of a cannula extending through the sealing and elastic sheets, for administering local anesthetics or other medicines adjacent the wound.

BRIEF DESCRIPTION OF THE DRAWINGS

FIG. 1 is a cross section, partially broken away, illustrating the apparatus of the present invention.

FIG. 2 is a top plan view illustrating the sealing member portion of the apparatus shown in FIG. 1.

FIG. 3 is a bottom plan view of the elastic member portion of the apparatus shown in FIG. 1.

FIGS. 4, 5 and 6 progressively illustrate steps in the method, as well as the apparatus utilized with the invention.

FIG. 7 is a cross-sectional elevation of the apparatus of the present invention.

FIG. 8 is a cross-sectional elevation, partially broken away, illustrating an alternative form of the present invention.

FIG. 9 is a cross-sectional elevation, partially broken away, illustrating an alternative form of the present invention including a medicine administrating feature.

FIGS. 10 and 11 are top plan views illustrating an alternative use for the apparatus of the present invention when the edges of the surgical wound are to be formed in elliptical pattern.

FIG. 12 is a top plan view of an alternate embodiment of the sealing sheet illustrated in FIG. 2.

DETAILED DESCRIPTION OF THE INVENTION

A detailed description of the preferred embodiments of the present invention will now be described with reference to the drawing.

A first embodiment of the apparatus is shown in FIGS. 1, 2 and 3. The apparatus is provided with an elastic member 10, comprising an elastic sheet 12 which, in this example, is a closed-cell, polyvinyl chloride foam having a cell diameter of not greater than about 1/32 of an inch, and preferably on the order of 1/64 of an inch. A suitable foam is manufactured by Uniroyal under the trademark Ensolite. The foam sheet 12 is treated with a vinyl-nitrile extender to impart high elasticity and elastic memory characteristics. The foam sheet 12 is substantially impervious and non-absorptive to blood and other body fluids emitted from a surgical wound, and has a sufficient non-tear and elastic memory characteristic to be capable of withstanding stretching to about twice the original dimensions of the sheet 12.

As discussed in greater detail below with reference to FIG. 7, an elastic silicone sheet 40 may be substituted for the elastic foam sheet 12 in FIG. 1 when translucency is an important requirement for the particular surgical procedure being undertaken. However, when the PVC foam sheet 12 is utilized, it preferably has a thin polyurethane film 14 across its upper surface. The top of the upper polyurethane film defines an exposed surface 15, to which a sealing sheet 20 may be attached.

As is illustrated in FIGS. 1 and 3, the bottom of the elastic sheet 10 is provided with an adhesive layer 18. The adhesive layer 18 is preferably selected to provide the following characteristics: a high degree of elasticity in order to expand and contract with the elastic sheet 12; a low vapor-fluid transmission rate, that is, being substantially impervious to blood and other body fluids from the surgical wound; and being sufficiently aggressive to adhere to a patient's skin during stretching of the elastic sheet 12, and for a period of days thereafter. A specific adhesive which is suitable for this purpose is manufactured by Adhesives Reasearch, Inc., and is identified by the mark ARclad DEV-7125; this adhesive is highly elastic and has a peel strength of about 2,000 grams in a 90 degree peel test. Other equivalent adhesives are suitable as well. When the elastic sheet is formed of transparent silicone, as described above, then a transparent adhesive is necessary. A suitable silicone adhesive for this purpose is manufactured by Dow Corning as adhesive number 355, which has a peel strength on the order of 1,600 grams in a 90 degree peel test.

Referring now to FIGS. 1 and 3, the apparatus of the present invention is also provided with a sealing member 20. The sealing member 20 comprises a sealing sheet 22 which is relatively inelastic with respect to the elastic sheet 12, and which has a highly aggressive adhesive layer 24 across its bottom surface in order to adhere to the upper, exposed surface 15 of the elastic member 10. A suitable material for the sealing sheet 22 is a semi-rigid polyurethane approximately 0.050 inches thick, and having a durometer rating of about 85 on the durometer "A" scale.

The sealing member 20 is provided with holes 26 extending completely therethrough, to permit blood and other body fluids to drain without creating pockets between the elastic and sealing members 10 and 20, respectively. As shown in FIG. 2, each hole 26 laterally overlaps the next adjacent hole, with plural rows of holes being provided to insure proper drainage from a wound irrespective of where the wound is located under the sealing member 20.

The particular adhesive selected for the layer 24 is chosen to provide a high degree of adhesive agressiveness (and being preferably more aggressive than the adhesive layer 18). It is also preferred that the sealing member 20 be initially removable, to permit the physician to first position the sealing member 20 over the elastic member 10, and if the sealing member 20 is improperly positioned or if the skin at the wound site is improperly reapproximated, then the sealing member 20 may be removed from the elastic member 10 and the procedure reinitiated. This may be achieved with an adhesive at layer 24 which is pressure sensitive. Preferably, this adhesive has a peel strength on the order of 3,000 grams in a 90 degree peel test.

The term "aggressive" as applied to an adhesive generally, and specifically to the adhesive layers 18 and 24, refers to the adhesive's shear, peel and tack characteristics. Shear is defined as the amount of stress before the adhesive disassociates from itself; peel refers to the adhesion longevity; and tack refers to the initial grip characteristics of the adhesive.

A description of the manner in which the apparatus shown in FIGS. 1-3 is utilized to facilitate the opening and closing of a surgical wound will now be described with reference to FIGS. 4-6.

Noting FIG. 4, a patient 30 is prepared for surgery at a treatment site 31 on the patient's body. Initially, the surgeon selects an elastic member 10 having dimensions suitable for the particular surgical procedure to be undertaken, and then adheres the adhesive layer 18 to the treatment site 31. The surgeon then forms a cut 19 completely through the elastic member 10 and through the patient's skin 34 to form a surgical wound 32 (FIG. 5). In selecting the elastic member 10 and making the incision, the surgeon leaves uncut the end areas 13 and 17.

Thereafter, the skin 34 at the treatment site 31 is retracted by retractor arms 36 and 38 so as to create a greater opening for the surgical procedure in the wound 32. As is shown in the top view of FIG. 5, the retractors 36 and 38 substantially stretch both the skin and the elastic sheet 12, which are stretched together.

Under certain septic conditions, it may be necessary to leave the surgical wound 32 open for a substantial period of time prior to closing. Such situations occur in the case of gunshot wounds, ruptured appendix, a perforated colon diverticulum or ulcer, or similar conditions in which the wound is rendered potentially infected. The elastic sheet 12 and the adhesive 18 are specifically selected to be retractable with the patient's skin 34 under those conditions for a substantial period of time, and to have a sufficient elastic memory to return with the skin to the approximate position of the skin before surgery, when wound closure is undertaken with the elastic member 10, as described next.

FIG. 6 illustrates the manner in which the edges of the wound are reapproximated, and the wound is closed. As there shown, the cut 19 in the elastic member 10 is reapproximated to the original position, with the underlying cut edges of the skin 34 also being reapproximated, because of the close adherence between the member 10 and the skin 34. The surgeon then applies the sealing member 20 over the exposed surface 15 of the elastic member 10, bridging both the cut 19 and the uncut areas 13 and 17. As was noted previously, the adhesive layer 24 is preferably initially removable, so that the sealing member 20 may be first lightly fixed to the upper surface 15 of the elastic member 10. It will be appreciated that the surgical staff achieves reapproximation of the cut 19 and the skin 34 by pushing the skin and the elastic member 10 together at the treatment site 31; after application of the sealing member 20 (but before pressure is applied to firmly seal the adhesive layer 24) the skin at the treatment site 31 may be released, to determine if proper reapproximation of the wound has been achieved. If not, the releasable characteristics of the adhesive layer 24 will permit substantial removal of the sealing member 20, without substantial difficulty. Thereafter, the cut 19 and the skin 34 may be reapproximated, and the procedure continued until the desired positioning is achieved. The sealing member 20 may then be firmly adhered to the upper surface 15 of the elastic member 10.

As noted above, the adhesive layer 18 is selected so that it retains its adhering characteristics for a period of time following surgery sufficient to permit healing. After an adequate period, the elastic member 10 may then be peeled away from the patient's skin.

An alternative form of the elastic member for the apparatus of the present invention will now be described with reference to FIG. 7, in which the elastic member 40 comprises a transparent silicone sheet having substantially the same elasticity, non-tear and elastic memory characteristics as the sheet 12 illustrated in FIG. 1 and described above. The elastic sheet 40 has a transparent adhesive layer 42 across its bottom surface. In this embodiment, both the elastic sheet 40 and the sealing sheet 22, (as well as the respective adhesive layers 42 and 24) are transparent, in order to permit observation of the treatment site before the wound is opened, and of the wound after closure.

FIG. 7 also illustrates how the cut 49 and the wound 32 appears in cross section; it will be noted that the holes 26 in the sealing sheet 22 provide a path for the flow of blood and other body fluids from the wound 32 and through the cut 49 (and likewise the cut 19 shown in FIGS. 4-6), and thus avoids a degradation of the adhesive layers 18, 42 and 24, and further avoids substantial intrusion of those fluids into the closed-cell PVC foam sheet 12 illustrated in FIG. 1 above, or between the elastic and sealing sheets.

FIG. 8 illustrates an alternative form of the apparatus of the present invention, in which the elastic sheet 50 (like the sheet 12 in FIG. 1, or the sheet 40 in FIG. 7), has an adhesive 52 across its bottom surface. In this embodiment, the sealing member 60 comprises a relatively inelastic sheet having overlapping sides 68 dimensioned to fit closely over the longitudinal edges the elastic sheet 50. As shown in FIG. 8, the sealing member 60 likewise includes an adhesive layer 64, which is intended to adhere the sheets 50 and 60 together.

FIG. 9 illustrates an additional feature which may be utilized with the apparatus of the present invention. A cannula 70 is extended through the sealing and elastic members 20 and 10, and into the treatment site adjacent the wound. The cannula 70 includes an injection port 76, through which a needle 78 may extend to administer local anesthetics or other medicines.

FIGS. 10 and 11 illustrate the manner in which the apparatus of the present invention may be utilized for certain types of surgical wounds where the edges of the wound are not parallel, such as a wound where a substantial portion of the patient's tissue (as, for example a radical mastectomy) is to be removed.

Noting FIG. 10, the tissue portion to be removed is designated by the reference numeral 80. Two strips 86 and 90 are provided, each of which is comprised of materials like the elastic member 10 in FIG. 1 (or alternatively the sheet 40 in FIG. 7), and each of which has an adhesive like the adhesive layer 18 across the bottom surface and in contact with the patient's skin. The strips 86 and 90 are disposed on the patient's skin and around the area of tissue 80 to be removed, with a peripheral edge of each strip 86, 90 overlapping and parallel with the line where an adjacent surgical incision is to be made, as defined by dotted lines 82 and 84 in FIG. 10. Each strip 86, 90 has opposing ends 87, 88 and 91, 92 respectively. The surgeon conducts the surgical procedure for removing the tissue 80 by cutting along the lines 82 and 84 and through the strips 86 and 90, thereby defining the edges of the surgical wound. To close the wound, the two strips 86, 90 are brought together (note FIG. 11). A sealing member 20 is then placed over the top surface of the elastic strips 86, 90 so as to retain the cut edges of the wound and the peripheral edges of the two closure strips 86, 90 while the wound heals.

An alternative form of the sealing member 20 of FIGS. 1 and 2 is shown in FIG. 12. In this embodiment, the sealing member, referred to by reference numeral 21 in FIG. 12, has oblong slits 27 in place of the holes 26 shown in FIG. 2. The slits 27 achieve the same objective as the holes 26, by insuring that a series of drainage openings are located over the wound, even when the wound is not underneath the centerline of the sealing member 21.

It will be appreciated by those skilled in the art that the apparatus and method described allow the opening and closing of surgical wounds in a facile manner, without the use of sutures, staples or the like so as to achieve the objectives discussed above.

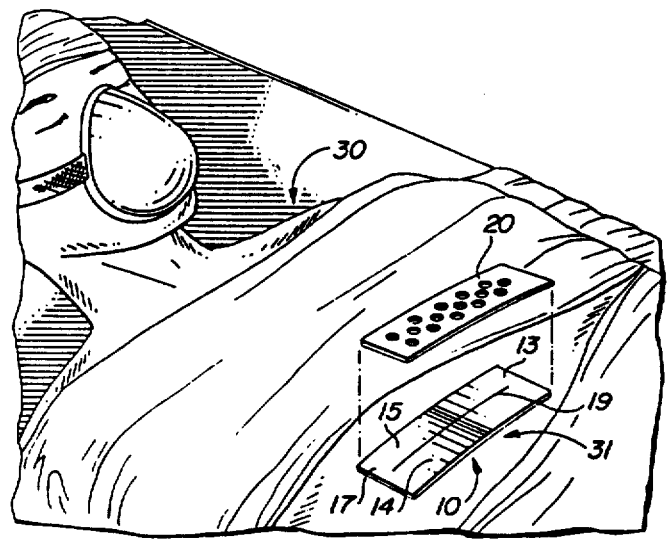

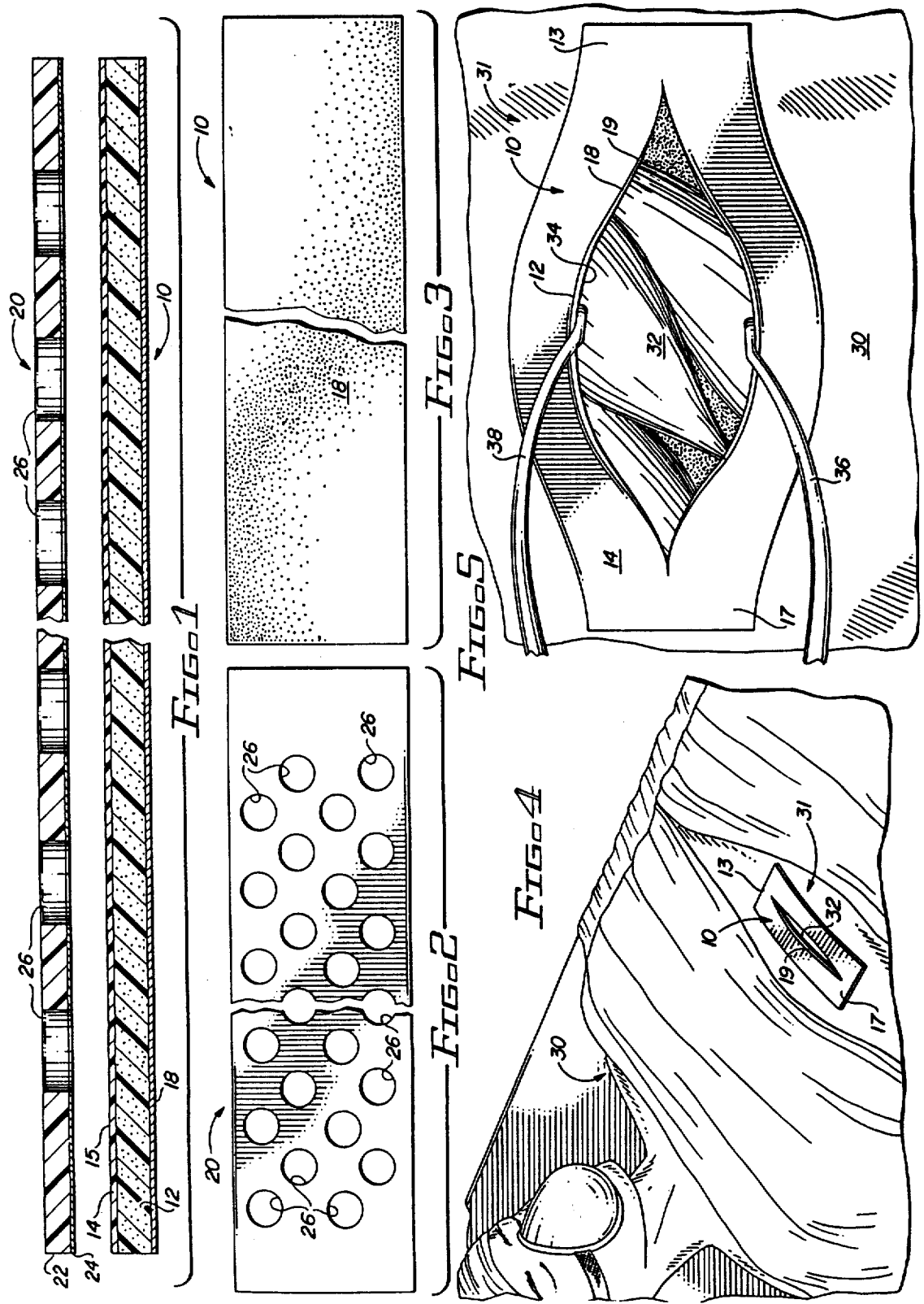

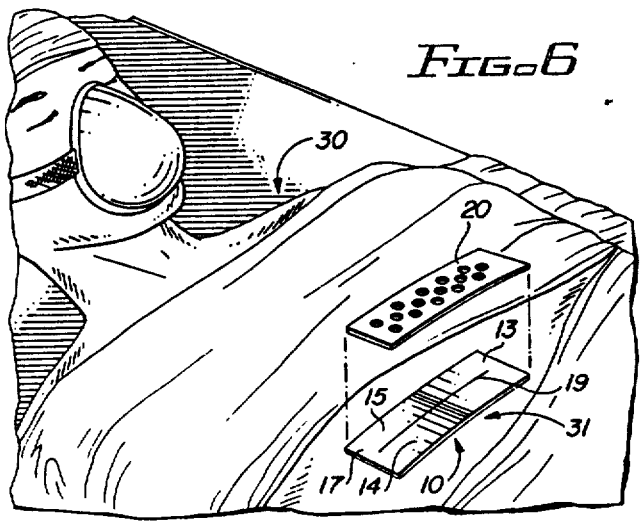
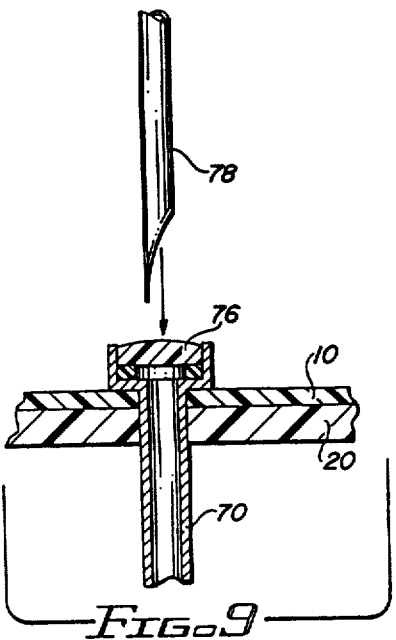
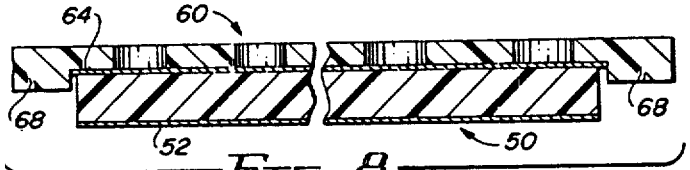
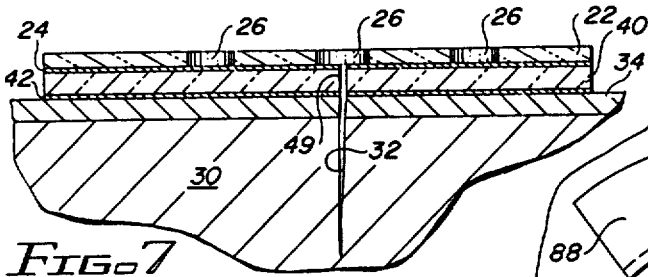
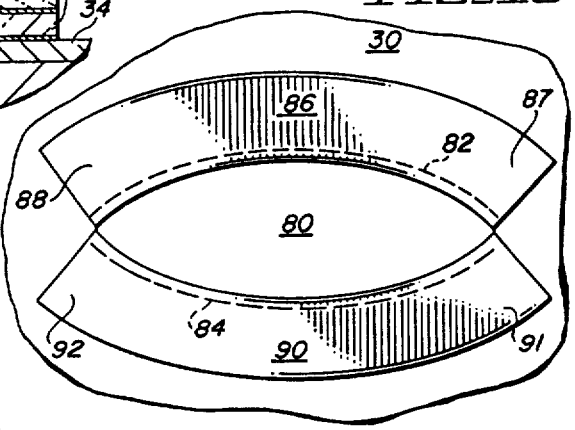
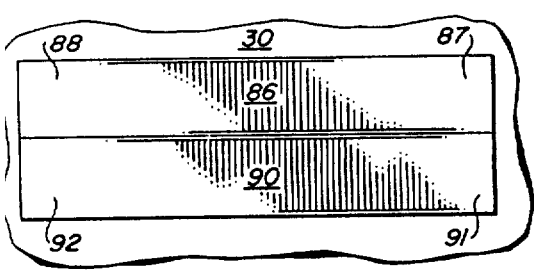
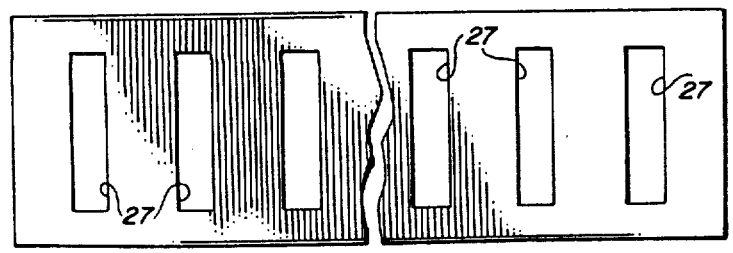

What is claimed is:

1. Apparatus for use in facilitating the opening and closing of surgical wounds, comprising:
    an elongated member having an elastic memory, the elastic member being substantially non-absorptive to blood and body fluids and having an adhesive disposed along one surface thereof; and
    an elongated, relatively inelastic sealing member dimensioned to overlay the elastic member and having an adhesive along one surface thereof for adhering the sealing member to a second surface of the elastic member opposite from its one surface.

2. The apparatus recited in claim 1 wherein the sealing member comprises a flat sheet of a plastic material.

3. The apparatus recited in claim 2 wherein the sealing member adhesive is initially releasable, so that the sealing member may be removed for repositioning before final sealing.

4. The apparatus recited in claim 2 wherein the sealing member is transparent.

5. The apparatus recited in claim 4 wherein the adhesive along the one surface of the elastic member is sufficiently elastic for retraction with any skin to which the adhesive is attached.

6. The apparatus recited in claim 1 wherein the elastic member comprises a closed-cell foam having an elastic extender contained therein.

7. The apparatus recited in claim 6 wherein the closed-cell foam has a cell size not greater than 1/32 of an inch in diameter.

8. The apparatus recited in claim 6 further comprising a high density layer across the second surface of the elastic member.

9. The apparatus recited in claim 1 wherein the elastic member has a non-tear and elastic memory characteristic capable of withstanding stretching to about twice the original dimensions.

10. The apparatus recited in claim 1 wherein the elastic member adhesive has an adhesive characteristic which lasts for a period sufficient to permit healing, and wherein the sealing member adhesive has a greater adhesive characteristic than the elastic member adhesive.

11. The apparatus recited in claim 1 wherein the sealing member has a durometer rating on the order of about 85.

12. The apparatus recited in claim 1 further comprising a cannula extending through the sealing member and dimensioned for administering a medicine adjacent the wound.

13. Apparatus for use in the closing of a surgical wound and for maintaining the wound closed for an extended period to facilitate healing, comprising:
an elongated sheet of an elastic material having an elastic adhesive along one surface thereof, the elastic material having an elastic memory and being relatively impervious to blood and body fluids;
an elongated sealing sheet dimensioned to fit across an exposed surface of the elastic sheet, the sealing sheet being inelastic relative to the elastic sheet and having an adhesive along one surface thereof for engaging and adhering the sealing sheet to the exposed surface of the closure sheet; and wherein
the sealing sheet adhesive is sufficiently aggressive to hold segments of the elastic sheet together for the extended period to facilitate wound healing without sutures, staples or other devices extending into the patient's body.

14. The apparatus recited in claim 13 wherein the elastic sheet has a non-tear characteristic capable of withstanding stretching and expansion to about twice its original dimensions, and the elastic memory characteristic is capable of returning the elastic sheet to substantially the original dimensions after deformation for several days.

15. The apparatus recited in claim 13 wherein the sealing sheet adhesive is initially releasable.

* * * * *

UNITED STATES PATENT AND TRADEMARK OFFICE
CERTIFICATE OF CORRECTION

PATENT NO. : 5,026,389

DATED : June 25, 1991

INVENTOR(S) : Thieler

It is certified that error appears in the above-identified patent and that said Letters Patent is hereby corrected as shown below:

The title page should be deleted and replaced with the attached title page.

The drawing sheets consisting Figure 1-12 should be added as shown on the attached pages.

Signed and Sealed this

Seventh Day of December, 1993

Attest:

BRUCE LEHMAN

Attesting Officer     Commissioner of Patents and Trademarks

United States Patent [19]

Thieler

[11] Patent Number: 5,026,389
[45] Date of Patent: Jun. 25, 1991

[54] METHOD AND APPARATUS FOR OPENING AND CLOSING SURGICAL WOUNDS

[76] Inventor: William R. Thieler, 2175 Via Tuscany, Winter Park, Fla. 32789

[21] Appl. No.: 604,059

[22] Filed: Oct. 26, 1990

Related U.S. Application Data

[62] Division of Ser. No. 225,377, Jul. 28, 1988, Pat. No. 4,966,605.

[51] Int. Cl.$^5$ .............. A61B 17/00; A61L 15/00
[52] U.S. Cl. ......................... 606/215; 128/156
[58] Field of Search ............ 606/214, 215, 216; 128/155, 156

[56] References Cited

U.S. PATENT DOCUMENTS

| | | | |
|---|---|---|---|
| 2,018,517 | 10/1935 | Fetter | 606/215 |
| 2,421,193 | 5/1947 | Gardner | 606/215 |
| 2,735,426 | 2/1956 | Claydon | 128/156 |
| 3,060,932 | 10/1962 | Pereny et al. | 606/215 |
| 3,349,765 | 10/1967 | Blanford | 128/156 |
| 3,520,306 | 7/1970 | Gardner et al. | 606/215 |
| 3,921,627 | 11/1975 | Wilson | 128/156 |
| 4,370,981 | 2/1983 | Sanderson | 606/215 |
| 4,531,521 | 7/1985 | Haverstock | 606/215 |
| 4,653,492 | 3/1987 | Parsons | 128/155 |
| 4,743,232 | 5/1988 | Kruger | 128/156 |

*Primary Examiner*—Stephen C. Pellegrino
*Assistant Examiner*—Gary Jackson

[57] ABSTRACT

A surgical method and apparatus for opening and closing surgical wound utilizes an elastic member which is adhered across the patient's skin at the treatment site. The wound is opened by cutting through the elastic member and through the patient's skin to permit a surgical procedure to be conducted. The wound is then closed by reapproximating the patient's skin at the treatment site and by bringing the cut edges of the elastic member together and adhering a relatively inelastic sealing member over the elastic member to maintain the cut edges while the wound heals.

15 Claims, 2 Drawing Sheets